(12) United States Patent
Nacson et al.

(10) Patent No.: US 7,421,912 B2
(45) Date of Patent: Sep. 9, 2008

(54) SAMPLING DEVICE

(75) Inventors: Sabatino Nacson, Thornhill (CA); Yuri Wiseman, Thornhill (CA); Dragoljub Ridjosic, Mississauga (CA); Sergey Kapitoulsky, Toronto (CA)

(73) Assignee: Smiths Detection, Inc., Ontario (CA)

( * ) Notice: Subject to any disclaimer, the term of this patent is extended or adjusted under 35 U.S.C. 154(b) by 78 days.

(21) Appl. No.: 11/303,016

(22) Filed: Dec. 16, 2005

(65) Prior Publication Data

US 2007/0137319 A1  Jun. 21, 2007

(51) Int. Cl.
*G01N 1/22* (2006.01)
(52) U.S. Cl. .............................................. 73/864
(58) Field of Classification Search .............. 73/864, 73/864.32, 864.81, 864.91; 422/99, 104, 422/63
See application file for complete search history.

(56) References Cited

U.S. PATENT DOCUMENTS

| | | | | |
|---|---|---|---|---|
| 3,970,428 | A | 7/1976 | Barringer | 73/863.22 |
| 4,192,176 | A | 3/1980 | Barringer | 73/28.04 |
| 4,220,414 | A | 9/1980 | Barringer | 356/318 |
| 4,909,090 | A | 3/1990 | McGown et al. | 73/864.33 |
| D329,391 | S | 9/1992 | Bromberg et al. | D10/81 |
| 5,212,991 | A | 5/1993 | Suzanne et al. | 73/863.11 |
| 5,425,263 | A | 6/1995 | Davies et al. | 73/28.05 |
| 5,476,794 | A | 12/1995 | O'Brien et al. | 436/92 |
| 5,571,976 | A | 11/1996 | Drolet | 73/864.71 |
| 5,741,984 | A * | 4/1998 | Danylewych-May et al. | 73/864.71 |
| 5,846,487 | A * | 12/1998 | Bennett, II | 422/58 |
| 5,859,375 | A | 1/1999 | Danylewych-May et al. | 73/864.71 |
| 5,942,699 | A | 8/1999 | Ornath et al. | 73/863.21 |
| 5,988,002 | A * | 11/1999 | Danylewych-May et al. | 73/864.71 |
| 6,324,927 | B1 | 12/2001 | Ornath et al. | 73/864.33 |
| 6,358,743 | B1 | 3/2002 | Fox | 436/8 |
| 6,919,143 | B2 * | 7/2005 | Hwang et al. | 429/231.95 |
| 2002/0187076 | A1 | 12/2002 | DiCesare et al. | 422/99 |
| 2003/0203492 | A1 * | 10/2003 | Sillman | 436/46 |
| 2005/0036916 | A1 * | 2/2005 | Thomas et al. | 422/99 |
| 2005/0155440 | A1 * | 7/2005 | Kanjilal et al. | 73/864.32 |

FOREIGN PATENT DOCUMENTS

CA  2190070  5/1998

OTHER PUBLICATIONS

International Search Report dated Sep. 17, 2007 (4 pgs.).

* cited by examiner

*Primary Examiner*—Hezron E. Williams
*Assistant Examiner*—Tamiko Bellamy
(74) *Attorney, Agent, or Firm*—Foley & Lardner LLP

(57) ABSTRACT

A sampling apparatus and method of obtaining a sample are provided. The apparatus has a body, a head connected to the body, and a mechanism for retaining a substrate on the head. The apparatus enables an area to be sampled quickly and efficiently, while minimizing cross-contamination of a sample and incorrect placement of a sample in an analyzer.

24 Claims, 11 Drawing Sheets

SAMPLING DEVICE

BACKGROUND

Trace detection has various important applications, such as, for example, screening of individuals and baggage at transportation centers, facility security, military applications, forensic applications, and cleaning validation.

Modern detection equipment can detect target compounds in the nanograms to picograms range, but effective detection requires obtaining a suitable sample. Various sampling methods are known and mainly involve vapor and particle sampling. For example, U.S. Pat. No. 4,909,090 teaches the use of hand operated vapour samplers which heats the surface to assist in dislodging vapours, which are trapped on collector surfaces in the probe. However, because some target compounds have low vapor pressures, this method can have somewhat limited usefulness.

Particle collection methods are also known. Particle collection techniques include surface inspection by means of physical particle collection in minute amounts, the use of dust pan-brush arrangements, vacuum suction onto porous or semi-porous substrates, filters, membranes and the like, and the use of swabs, swipes, gloves, etc. U.S. Pat. Nos. 3,970,428, 4,220,414, 4,192,176, and 5,425,263 are directed to particle collection methods useful for forensics and surface geochemical exploration where trace metals and organometals can be useful as pathfinder indicators in mineral exploration activities. U.S. Pat. No. 5,476,794 describes collection of sample particles with a glove and the use of an intermediate step involving vacuum suction off the glove.

Another method for collecting trace particles involves insertion of a filter disk into a suction line of a vacuum cleaner unit to remove particles for analysis by suction. After a sufficient quantity of dust/material is collected, the filter disk or substrate is removed and presented to an analytical device. The filter disk is inserted into a thermal desorption device which is rapidly heated to volatilize the collected material. The heating process converts the trace particles to vapors for conventional chemical vapor analysis, such as, for example, IMS, mass spectrometer or gas chromatography or such other instrument. This method suffers from the disadvantage of vacuum cleaner contamination and requires manipulating a cumbersome vacuum cleaner to obtain a sample.

Collection media in the form of hand coverings, such as gloves, mitts and swipes have been used in various forms for particle collection, but these techniques often require an intermediate step that transfers the sample collected on the a glove or the like to the analytical device. One method involves exposure of the collection medium to a suction device to vacuum the glove or mitt, as described in U.S. Pat. No. 5,476,794. This method is time consuming and the vacuum transfer is inefficient, causing a loss of sample due to incomplete transfer from the collection medium. Additionally, vacuum suction devices are noisy, cumbersome, and require power to energize the suction motors. Even small vacuum sampling devices have relatively limited battery lives. Moreover, the suction device can be contaminated during transfer of a sample containing a target compound requiring thorough cleaning before the next use. Finally, often an even greater problem is created by the suction causing collection medium fibers and lint to be released which can either obstruct the analytical device, present interfering chemicals or fluff/lint which might compete in the analytical process, as for example, if ion mobility spectrometer (IMS) is used where matrix effects from the hand covering material can compete too aggressively in the ionization process.

U.S. Pat. No. 5,476,794 describes collection of particles where the particles are transferred from a sample collection glove to a collection probe, and the complete probe is inserted into the analyzer to vaporize the samples. This technique involves a complex sampling probe, which can be easily clogged by debris and lint from the sampling gloves.

Conventional sampling substrates, which are handheld and cover the fingers are also known for collecting particles from surfaces, where the material is inserted directly into the analytical device. These materials have the advantage of avoiding an intermediate transfer step and the use of a suction device. However, collecting samples by hand can result in contamination or incomplete collection of a sample due to insufficient pressure of the sampling substrate against the item being analyzed.

Moreover, conventional sampling substrates often rely on the operator to ensure that the sampling area of the substrate material (or "swab") is properly aligned within an analyzer (or "analytical device"), so that the portion of the substrate material containing the sample is actually analyzed by the analytical device. For example, in IMS it is necessary that the collected sample is properly aligned on the sample desorber such that the collected sample is desorbed and analyzed by the IMS. When the sample area of the substrate is not properly aligned within the analyzer, the collected sample cannot be completely desorbed. Therefore, the test results of the sample can be affected by how the sample area of the substrate is aligned within the analyzer.

SUMMARY

Thus, there is a need for a sample collecting device that is capable of collecting and transferring the sample to an analytical device without an operator's hands touching the sampling substrate, and which avoids operator error in collecting a sample and positioning the collected sample in an analytical device.

Accordingly, one embodiment provides a sampling device for collecting a sample on a substrate for analysis in an analyzer comprising a body and a sampling head arranged to hold the substrate, wherein the sampling device is arranged to be inserted into a sample receiving device so that the substrate is properly aligned within the analyzer for optimal or substantially optimal introduction of the sample into the analyzer.

Another embodiment provides a method of collecting a sample comprising mounting a substrate in a hand held sampling device that includes a body and a sampling head arranged to hold the substrate, wherein the sampling device is arranged to be inserted into an analyzer so that the substrate is properly aligned within the analyzer for optimal or substantially optimal introduction of the sample from the substrate, manipulating the sampling device so that the substrate contacts a surface of interest, and inserting the sampling head into the analyzer for desorption and analysis of the sample.

It is to be understood that both the foregoing general description and the following detailed description are exemplary and explanatory only, and are not restrictive of the invention as claimed.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

DETAILED DESCRIPTION

A sampling device that avoids operator error is useful in collection of samples for analysis by an analytical device. The device solves operator error that can result in contamination of a sample, incomplete or ineffective sample collection, and incorrect placement of the collected sample within an analytical device.

Figure 7:
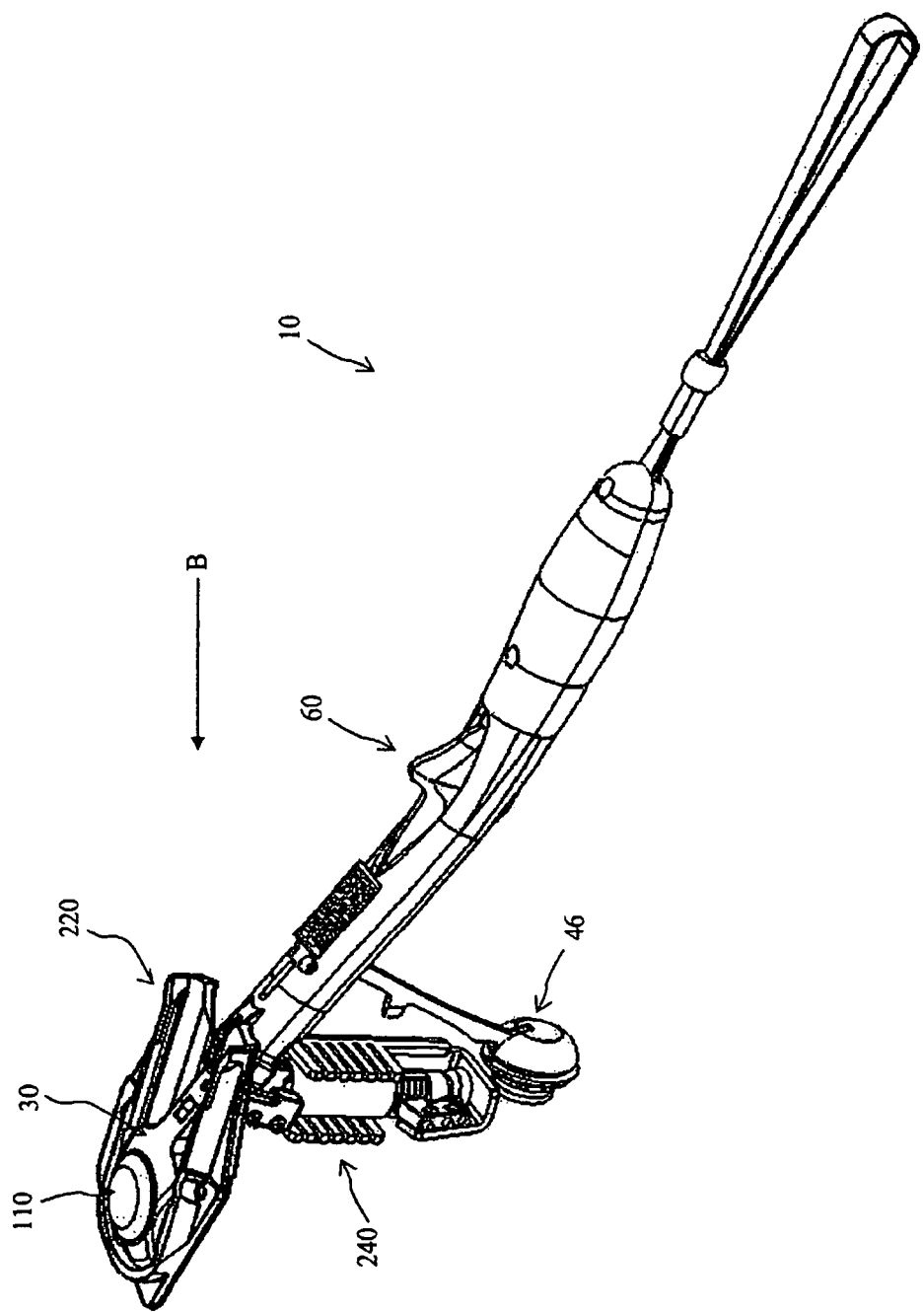
FIG. 7 is a perspective view of the sampling device of FIG. 1 inserted into an exemplary sample receiving device.

FIGS. 1-6 show an embodiment of a sampling device 10 for collecting a sample for analysis. This sampling device is capable of collecting samples for analysis without direct handling of the sampling substrate by the operator and eliminates operator error in collecting the sample. FIGS. 7-8 show an embodiment of a sampling device 10 positioned in a sample receiving device 220, which eliminates difficulties in positioning the sample collecting substrate in the analytical device such that the sample is properly aligned for effective analysis. FIGS. 8-11 show an embodiment of a sample receiving device 220 which is configured to receive a sampling device 10.

The sampling device 10 is can be configured so that an operator can manipulate the sampling device 10 to wipe, contact, or "swab" any item or subject of interest with the sampling area 110 of the sample collecting substrate 100, thus, collecting a sample from the item. For example, the sampling device can be used to collect samples from, for example, luggage, bags, packages, clothing, and individuals. In one embodiment, the device can be a handheld device.

Figure 1:
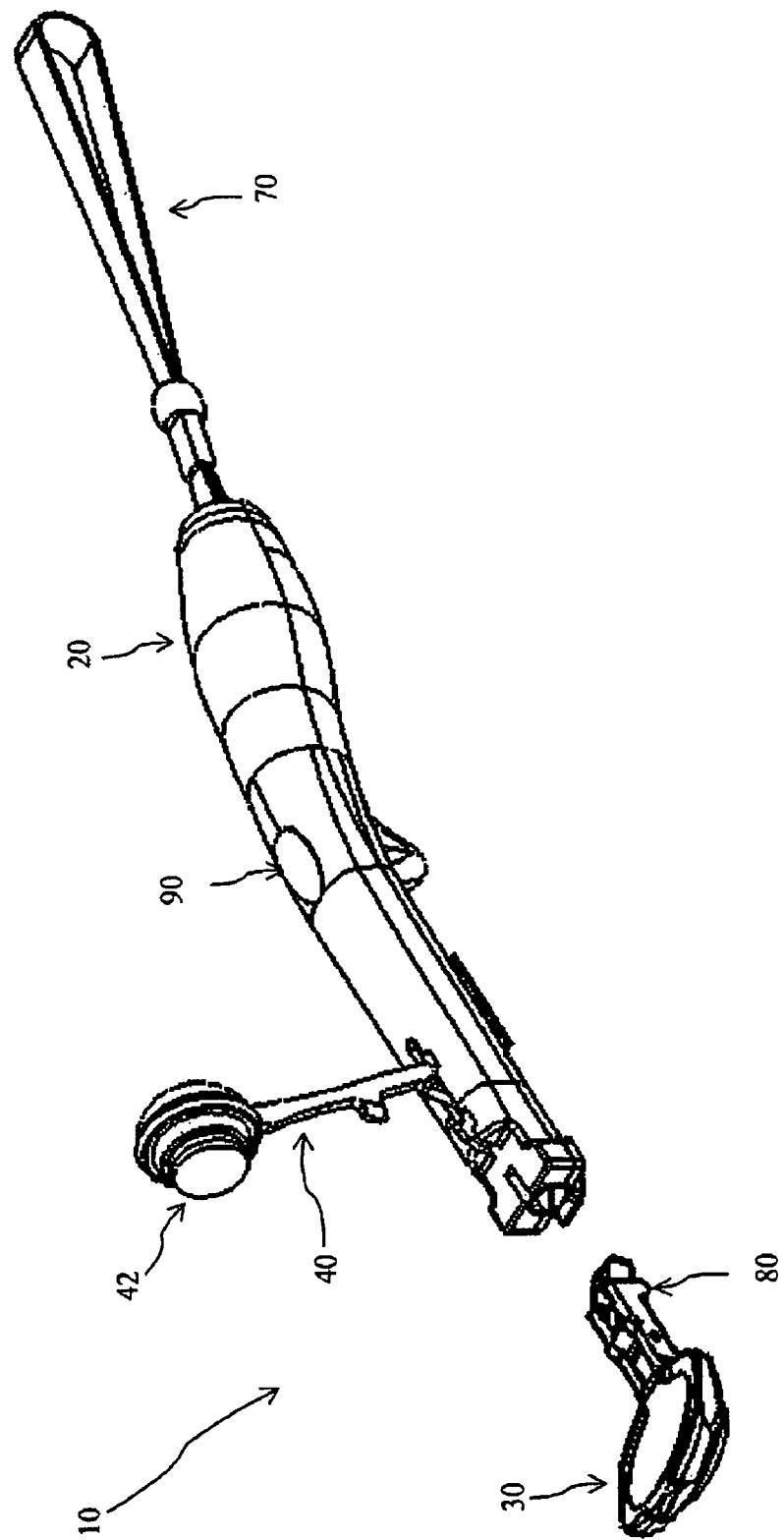
FIG. 1 is a partially exploded side perspective view of an exemplary sampling device.

FIG. 1 shows a sampling device 10 according to an embodiment. The sampling device 10 can be configured to provide a body 20 and a sampling head 30. The body 20 and sampling head 30 can be integral or detachable. The body 20 of the sampling device 10 can be grasped in the hand of an operator so that the sampling device 10 can be easily manipulated by the operator. The device can optionally include a strap 70 attached to the body 20 so that the sampling device 10 can be supported on the arm of an operator or hung by the strap when the sampling device 10 is not in use.

The sampling device 10 can use a replaceable sampling substrate 100 that can be held in the device using any suitable substrate retaining arrangement. The substrate 100 can be secured using, for example, a snap device, bezel, hook and loop, snap-fitting, or sandwich-type arrangement using a frame. For example, the sampling device 10 can include a sampling head 30, as shown in FIG. 1. For example, FIG. 6 shows a sample head 30 that is configured to support a substrate 100 so that a sample area 110 of the substrate 100 is arranged to collect a sample.

According to an embodiment, the sampling head 30 can include a sampling frame 120 for holding a substrate 100 within the sampling head 30. The sampling head can have any appropriate dimensions. For example, the sampling head 30 can have a length X from an end of the sampling head 30 to a center point of the substrate 100, and a diameter D. For example, the sampling head 30 can have an approximate length of 4 inches and an approximate diameter of 2 inches. The sampling frame 120 can include an upper member 122 and a lower member 124 so that the substrate 100 can be held between the upper member 122 and the lower member 124 (see FIG. 6). With this arrangement, the substrate can be easily installed and released from the sampling head 30. For example, the upper member 122 can be hinged to the lower member 124 by a pin 126 so that the upper member 122 can move relative to the lower member 124, allowing a substrate 100 to be removed from the sampling frame 120 and a new substrate 100 to be placed between the lower member 124 and the upper member 122. The upper member 122 can be fastened to the lower member 124, such as with a snap device, bayonet fastener, or any other attachment that can hold the substrate 100 in place. The sampling frame 120 can be arranged so that the sample area 110 of the substrate 100 is centered within the sampling head 30 for proper sample collection and thermal desorption.

The sampling head 30 can be constructed using any suitable material. In one embodiment, the material is capable of resisting deformation and degradation at temperatures of more than 300° C. for short periods of time, such as, for example, less than 90 seconds, 60 seconds, 30 seconds, 20 seconds, 10 seconds, 1 second, 0.5 second, or less than 0.25 second. In another embodiment, the sampling head can be comprised of steel, stainless steel, nickel super alloys, cobalt super alloys, chromized and/or galvanized and/or aluminized steel, aluminum or aluminum alloys, titanium or titanium alloys, ceramics, metal matrix composites, and carbon fiber composites. In a further embodiment, the sampling head is comprised of polyetheretherketone (PEEK). In an additional embodiment, the sampling head of comprised of black PEEK.

After collection of a sample, the sample can be analyzed. The sampling head 30 may be used for various methods of desorption of collected samples. For example, the sample can be vaporized using thermal desorption, infrared desorption, or desorption through other methods known in the art.

Figure 5A:
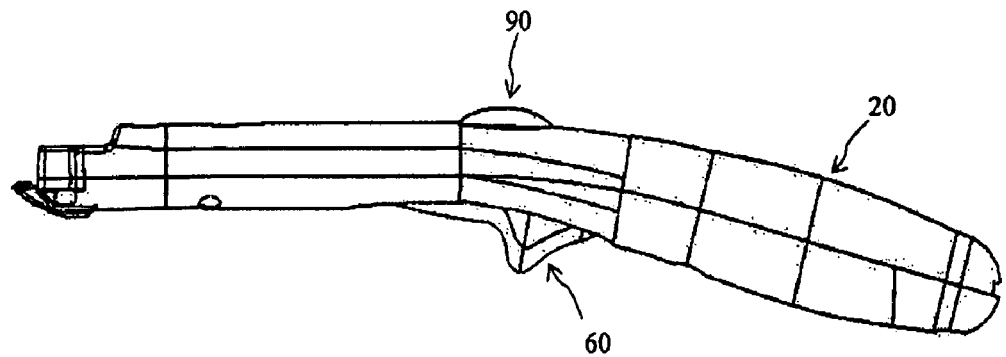
FIG. 5 shows (a) a side view, (b) an exploded perspective view, and (c) a front view of the external casing of the device of FIG. 1.
Figure 5B:
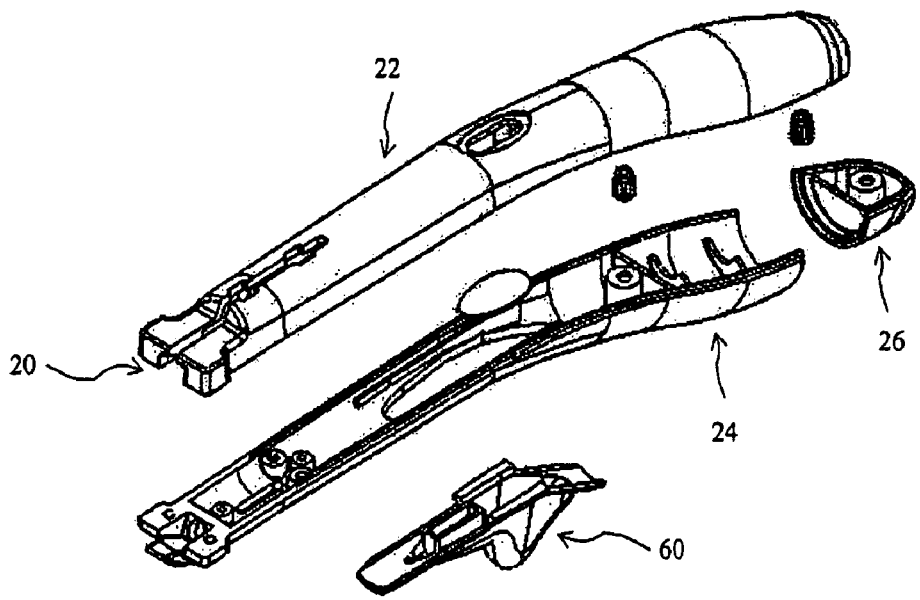

The sampling device 10 can also include a body, which is configured to receive a sampling head. The body can be any suitable configuration capable of receiving a sample head. FIG. 5(a) is a side view of the body 20 of the sampling device 10 according to an embodiment. FIG. 5(b) is an exploded view of the body 20 of the sampling device according to an embodiment, in which the body 20 includes an upper body portion 22, a lower body portion 24, and a member 26 for power supply, such as, for example, a battery. For example, as shown in FIG. 5(b), the body 20 can include an upper body portion 22 and a lower body portion 24 that are joined together, which can form a grip portion of the sampling device 10. The body can be composed of any suitable material, such as, for example, high temperature plastic materials, steel, stainless steel, and aluminum.

Figure 5C:
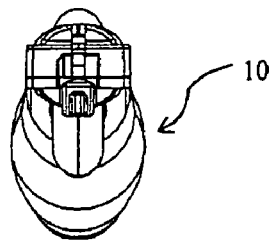
Figure 6A:
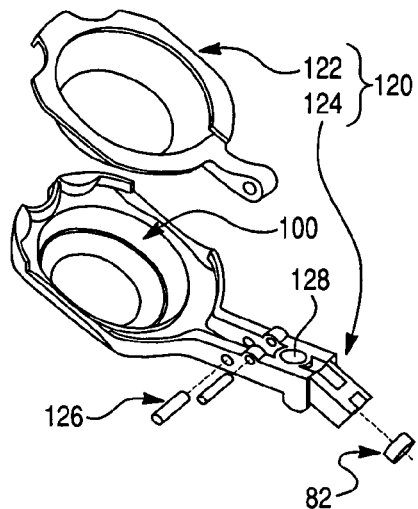
FIG. 6 shows (a) an exploded view of an exemplary sampling head, (b) a perspective view of the exemplary sampling head, (c) a perspective view of the bottom section of the sampling head, and (d) a bottom view of the sampling head, according to an embodiment.
Figure 6B:
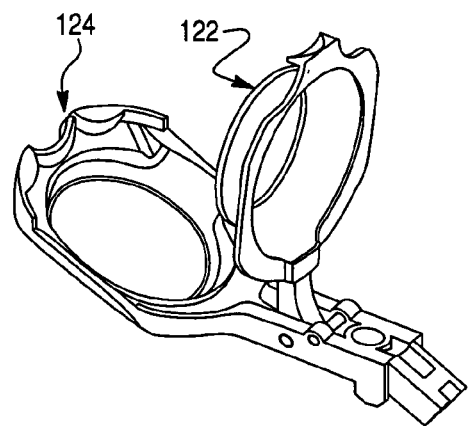
Figure 6C:
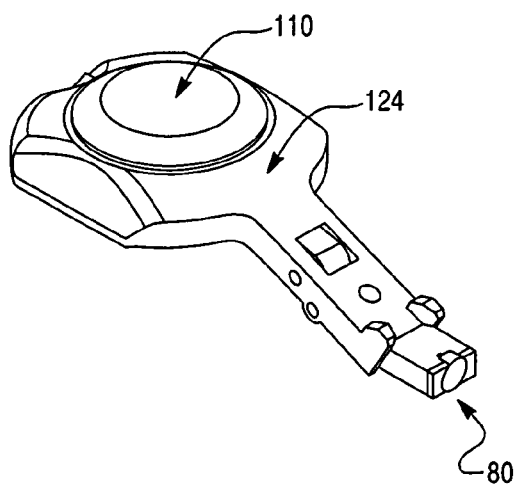
Figure 6D:
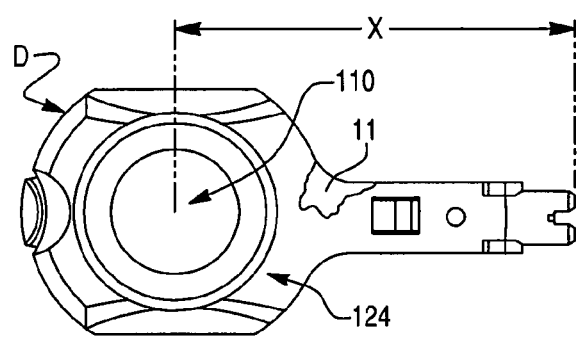

According to an embodiment, the sampling head 30 can be removed from the body 20 of the sampling device 10. FIG. 5(*c*) is an end view of the body 20 of the sampling device 10 according to an embodiment showing the mating feature where the sampling head 30 meets the body 20. The sampling head 30 can be attached to the body 20 by a connecting mechanism 80 can fasten the sampling head 30 to the body 20 of the sampling device 10 so that the connecting mechanism 80 can be readily attached to the body 20 of the sampling device 10 and detached from the body 20 of the sampling device 10. The connecting mechanism 80 can include any suitable fastening device 82 capable of fastening the sampling head 30 to the body 20 of the sampling device 10. Suitable fastening devices include, for example, a snap device, detent connection, bayonet fastener, interrupted thread, magnet, solenoid, or other fastening device known in the art. In one embodiment, the fastening device 82 can be a magnet. The connecting mechanism 80 can include a fastening device 82 in the sampling head 30 and a corresponding fastening device in the body 20 of the sampling device 10.

The device 10 can include a mechanism for engaging and disengaging the substrate retaining arrangement. For example, the body 20 can further include a trigger 60 for actuating a swing arm 40 that is associated with a swing head 30 that meets the sampling head 30 to hold a substrate 100.

In one embodiment, swing arm 40 can be provided for supporting a surface that contacts and/or shapes a substrate 100. In one embodiment, the sampling device 10 can include a swing arm 40 with a swing head 46. The swing head 46 can include a surface 42 that can be used to press against a surface of a substrate 100 so that the surface of the substrate 100 can be provided with a predetermined shape and support. The surface 42 of the swing head 46 can include a disk 44 that is attached to a swing head 46 (see FIG. 3(*a*)). The swing head 46 can be attached to the swing arm 40 so that the disk 44 is pressed against a surface of the substrate 100 when the swing arm 40 is forced downwards. The disk 44 can be integral with the swing head 46 or replaceable. In one embodiment, the disk 44 is replaceable by detaching the disk 44 from the swing head 46. For example, the disk 44 can be attached to the swing head 46 using any suitable means, such as, for example, an adhesive or Velcro. In another embodiment, the disk can be attached to the swing head with Velcro on one or more surfaces to enable easy replacement. The disk 44 can be any suitable rigid or elastomeric material, such as, for example, metal, polymer, ceramic, or composite. Suitable polymer materials include thermoplastic or thermasetting polymer and neat or filled polymer. In one embodiment, the disk 44 can be composed of silicone, latex rubber, or soft plastic material.

Figure 4:
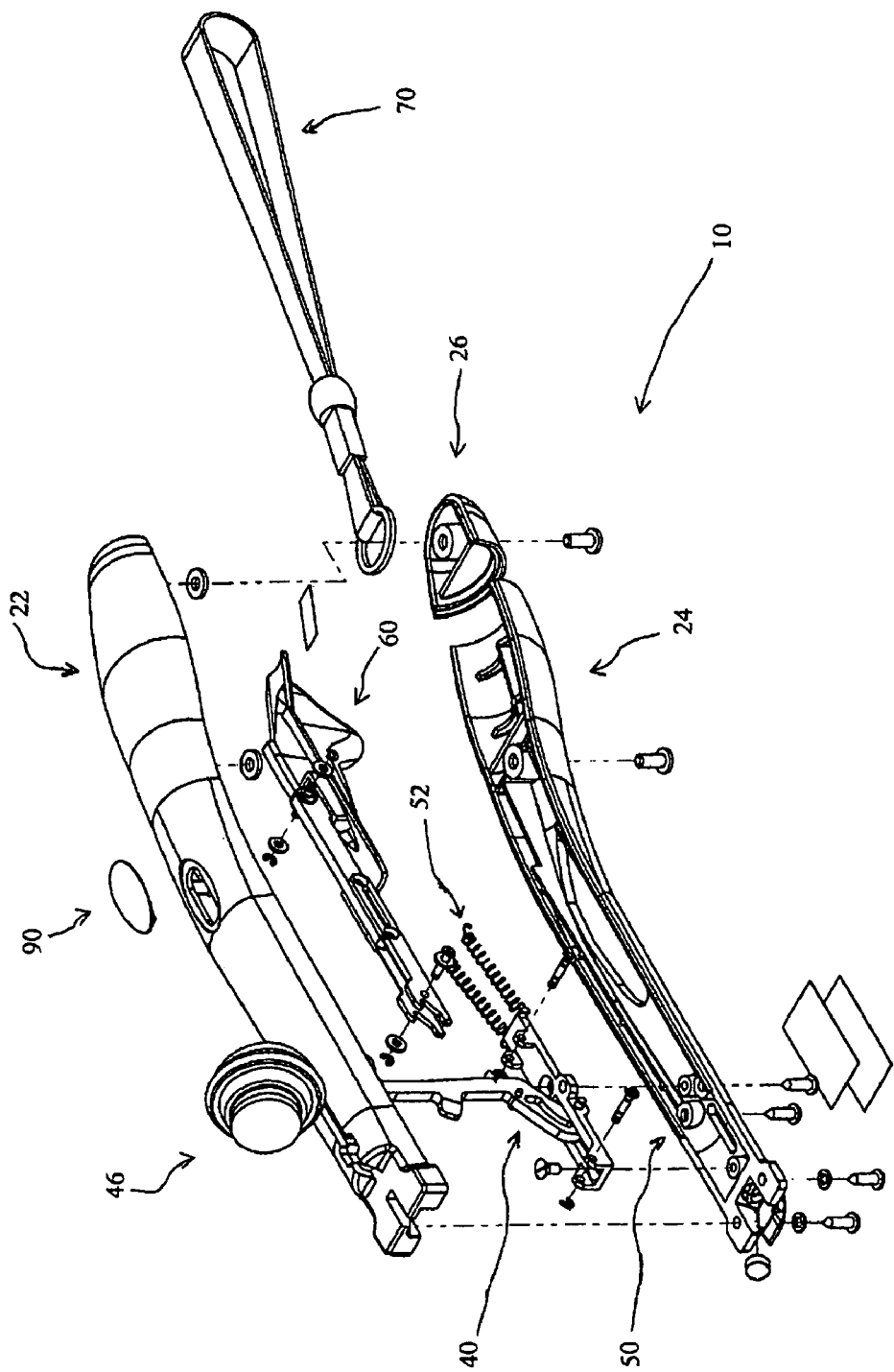
FIG. 4 is an exploded perspective view of the device in FIG. 3.

The swing arm 40 can include a device to control the movement of the swing arm 40 and to move the swing arm 40 and swing head 46 in the correct direction to apply a force to the substrate 100. For example, as shown in FIG. 4, the sampling device 10 includes a plunger 50 that presses the arm 40 such that the swing head 46 presses against a surface of the substrate 100. The plunger 50 can include a spring or a plurality of springs 52 that provides a force to press the swing arm 40 such that the swing head 46 presses against a surface of the substrate 100, or the spring or plurality of springs 52 can be arranged to move the swing arm 40 away from the swing head 46 when released from a locked position where the swing head 46 is engaged with the sampling head 30.

The swing arm 40 can be arranged to swing in a direction away from the sample head when the sampling head 30 is inserted into the analyzer 215 or to replace the substrate 100 in the sampling head 30, so that the swing arm 40 does not interfere manipulation of the sampling head 30. For example, the plunger 50 can be activated to move the swing arm 40 upwards into a position away from the sampling head 30. This operation of moving the swing arm 40 upwards and away from the sampling head 30 can be performed by an device that is activated by the operator. This device can be a trigger, lever, button, or other activating device known in the art and can be mounted on the body 20 of the sampling device. In the example shown in FIG. 4, the activating device is a trigger 60 that is pulled by the operator, causing the swing arm 40 to be moved upwards and away from the sampling head 30 against the force of the springs 52 or causing the swing arm 40 to be released from a locked position so that the force of the springs 52 moves the swing arm 40 upwards and away from the sampling head 30.

It can be desirable to detach the sampling head 30 during analysis of a sample. For example, the sampling head can be detached from the body 20 during analysis of a sample so that the body 20 can be used with other sampling heads to collect additional samples for analysis. In this fashion, multiple analyzers can be used with the sampling device 10 and the sampling heads 30.

According to an embodiment and as shown in FIG. 1, the sampling head 30 can be detached from the body 20 of the sampling device 10. With this arrangement, the sampling device 10 can be used to collect a sample by wiping or swabbing an object with a substrate 100, which is disposed within a sample head 30. After a sample is collected, and without removing the substrate 100 from the sampling head 30, the sampling head 30 can be can be inserted into an analyzer while the body 20 is retained for use with another sampling head 30.

Figure 2:
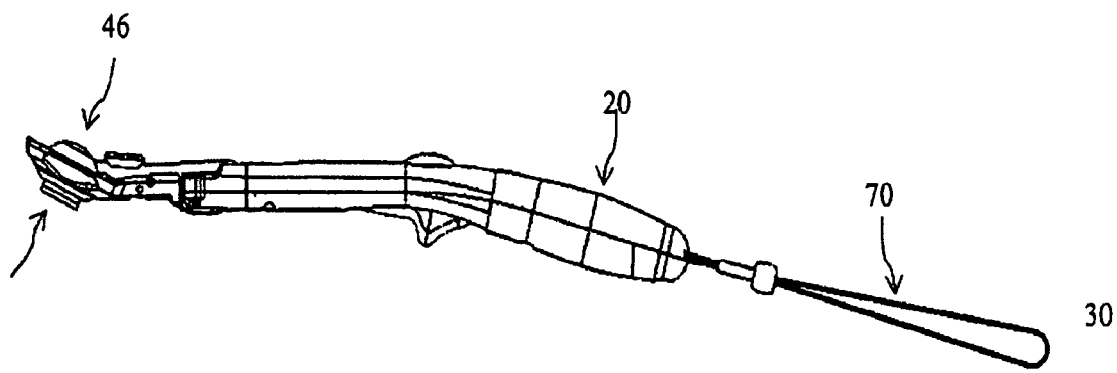
FIG. 2 is (a) a side view and (b) front view of the device in FIG. 1.
Figure 2:
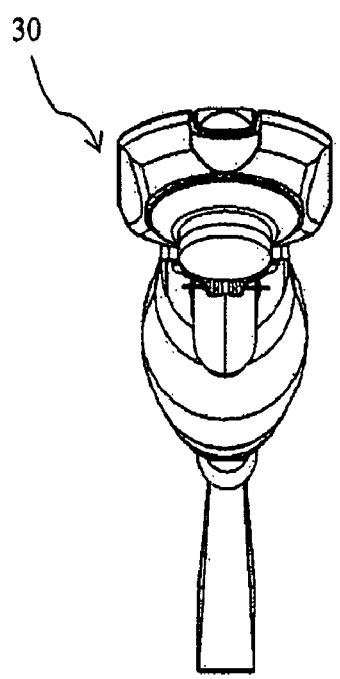
Figure 3:
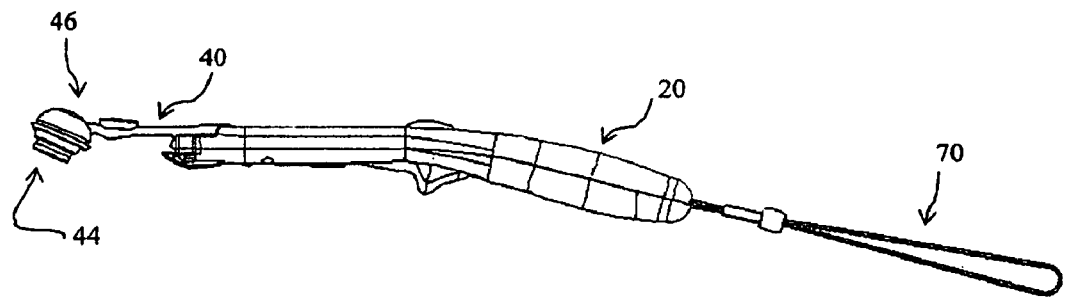
FIG. 3 is (a) a side view and (b) front view of the device in FIG. 1, with the sampling head removed to show the swing arm and swing head.
Figure 3:
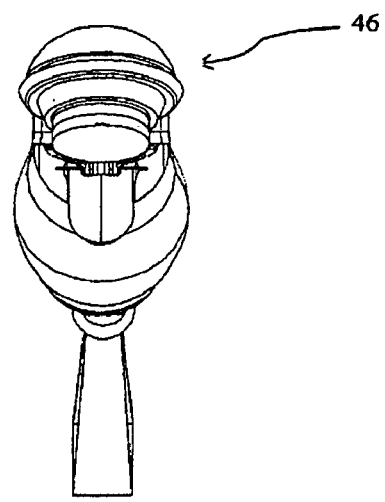

FIG. 3(*a*) shows a side view of the sampling device 10 according to an embodiment with the sampling head 30 removed. FIG. 2(*b*) shows an end view of the sampling device 10 with the sampling head 30 in place, according to an embodiment. FIG. 3(*b*) shows an end view of the sampling device 10 with the sampling head 30 removed according to an embodiment.

The sampling device 10 can be configured to engage with a sample receiving device, which is capable of receiving the sampling device 10. For example, the sample receiving device can be configured to receive the sampling head 30 in an orientation that is optimized for analysis of a collected sample.

Figure 9:
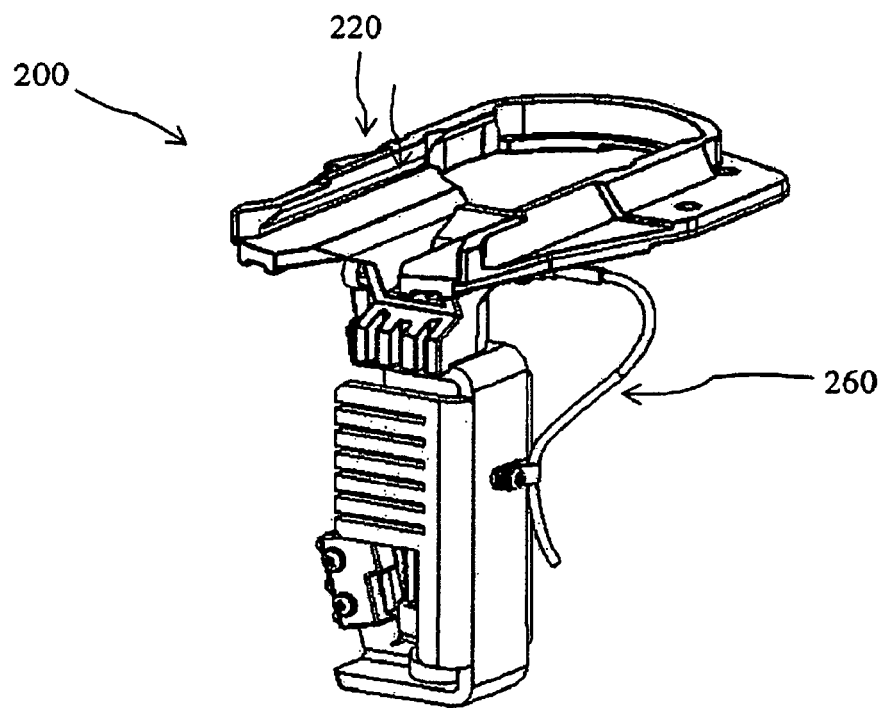
FIG. 9 is a perspective view of an exemplary sample receiving device.
Figure 11:
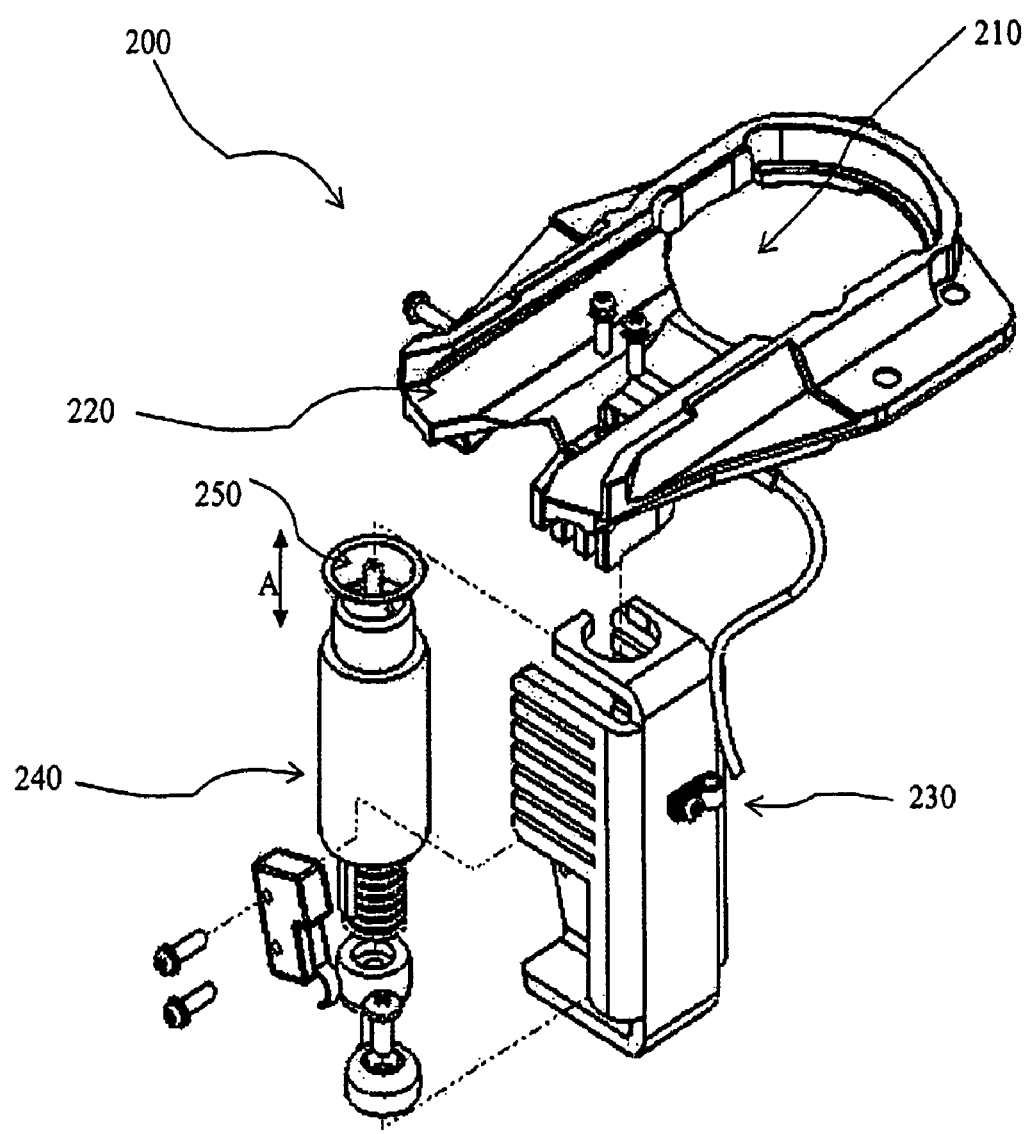
FIG. 11 is an exploded view of an exemplary sample receiving device.
Figure 12:
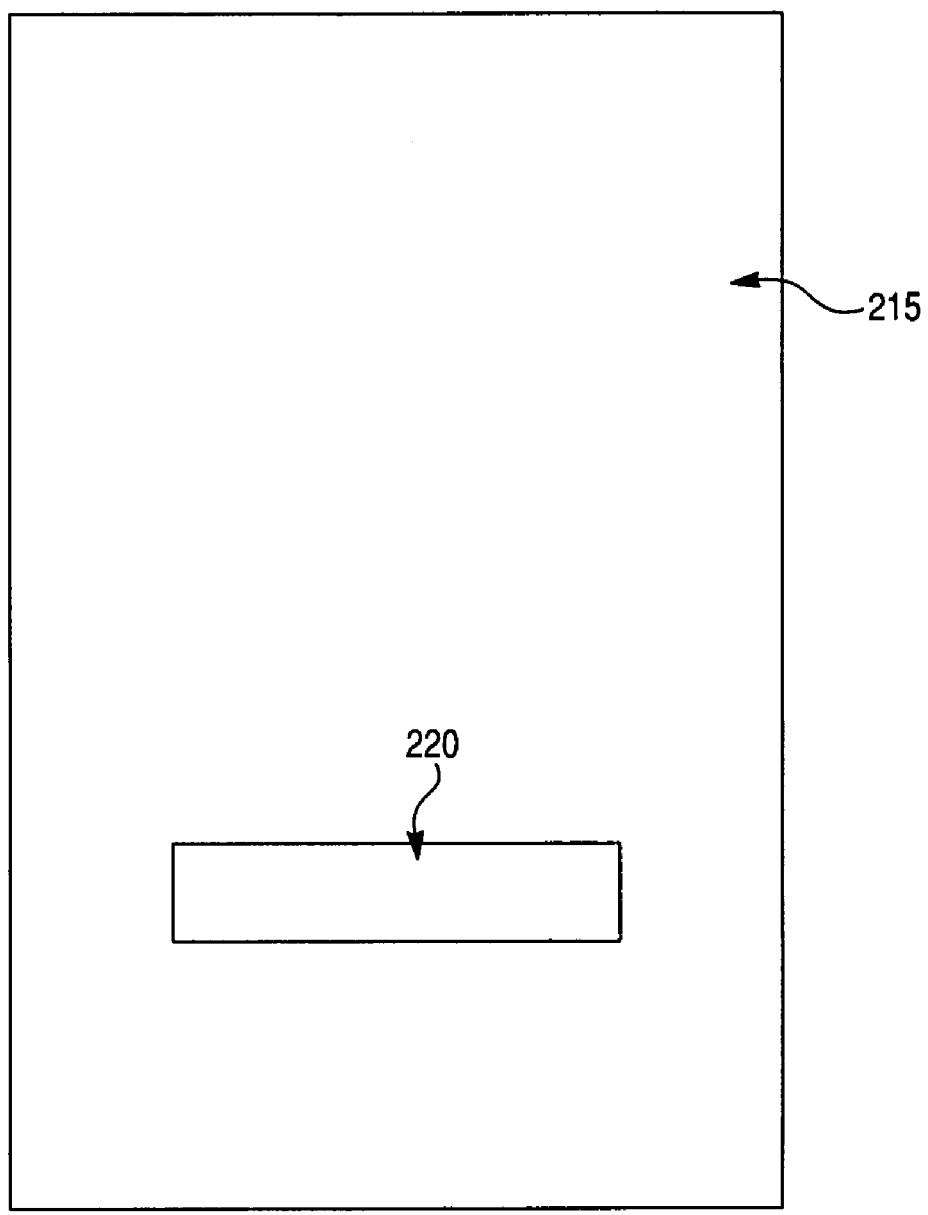
FIG. 12 is a black box diagram of an analyzer with a receiving device.

FIG. 11 is an exploded view of a sample receiving device 200, according to an embodiment. The sample receiving device 200 can be connected to, or part of an analyzer. The sample receiving device 200 includes a sample area position 210 where the sample area 110 of a substrate 100 is positioned for desorption and analysis. The sample area 110 of a substrate 100 can be positioned in the sample area position 210 by inserting the sampling head 30 of a sampling device 10 into the sample receiving device 200. The sample receiving device 200 can include a guide structure or plurality of guide structures 220 to guide and align the sampling head 30 within the sample receiving device 200, such as slots, rails, pins, slides, grooves, or any other suitable alignment structures known in the art. Such guide structures 220 to guide and align the sampling head 30 can correspond to the sampling head 30 dimensions so that the sampling head 30 is properly aligned and guided as the sampling head 30 is inserted into the sample receiving device 200. With this arrangement, the sample area 110 of the substrate 100 can be properly aligned within the analyzer so that the collected sample can be substantially or completely desorbed, providing accurate analysis of the sample. Furthermore, an operator is able to handle the substrate 100 using the sample device 10 during sample collection and analysis, minimizing cross-contamination and/or loss of samples. FIG. 9 shows a perspective view of the sample receiving device 200.

FIG. 7 shows a sampling device 10 with a sampling area 110 of a substrate 100 facing upwards and the swing arm 40 operated to move the swing head 46 away from the substrate 100 so that the swing head 46 will not interfere with insertion of the sampling head 30 within the sample receiving device 200. As shown in FIG. 7, once the sampling device 10 is arranged in this way, the sampling head 30 can be inserted into the slots 220 of the sample receiving device 200 and the sampling head 30 and sampling device 10 can be moved in the direction indicated by arrow B so that the sampling head 30 and sample area 110 are properly placed in the sample area position 210 and analysis of the collected sample can be performed. The sample receiving device 200 can be arranged in other ways so as to accept the sampling device 10 at different orientations as well, such as a sampling device 10 with the sample area 110 facing downwards.

Once the sample area 110 of the substrate 100 is aligned within the analyzer, the sample contained on the substrate 100 can be analyzed. In one embodiment, the substrate 100 can be heated. With this arrangement, proper alignment of the sample area 110 of the substrate 100 in the sample area position 210 is effected when the sampling device 10 is inserted into the sample receiving device 200, allowing accurate analysis of a sample. Once the sample is removed from the substrate the operator can reattach the sampling head 30 to the body 20 of the sampling device 10 and remove the sampling head 30 from the analyzer. Furthermore, while sampling head 30 and substrate 100 with a first sample are detached and placed within an analyzer for analysis, an operator can attach a second or other additional sampling head 30 to the body 20 of the sampling device 10 so that additional samples can be collected with the sampling device 10 while the first sample is analyzed. In one embodiment, insertion of a sampling head 30 into a sample receiving device 200 can cause the analyzer to begin analysis of the sample, thus requiring no additional action by the operator for analysis to begin. Alternatively, an operator can insert a sampling head 30 and then initiate sample introduction. Sample introduction can be by any suitable method, such as, for example, desorption. In one embodiment, a desorber is integral to the sample receiving device.

The above example describes the sample receiving device 200 as being used with a sampling device that has a detachable sampling head. However, the sample receiving device 200 can also be used with a sampling device having a sampling head that is integral with the body of the sampling device.

Figure 10:
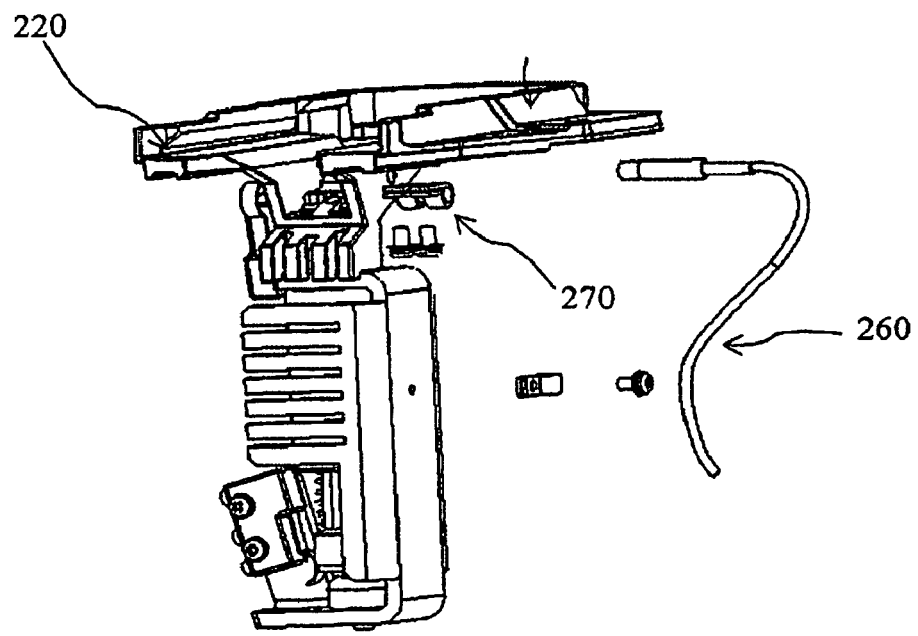
FIG. 10 is a perspective view of an exemplary sample receiving device with a control line in exploded view.

The sample receiving device 200 can include a locking mechanism 240 for locking the sampling head 30 in position within the sample receiving device 200 after the sampling head 30 has been received within the sample receiving device 200. The locking mechanism 240 can be positioned in the sample receiving device 200 by a locking mechanism housing 230. The locking mechanism 240 can include a locking device that engages with the sampling head 30 to retain the sampling head 30 within the sample receiving device 200 during sample analysis, or at least during introduction of the sample into the analyzer, maintaining the position of the sample area 110 of the substrate 100 in the sample area position 210. The locking mechanism 240 can be a pin, snap device, bayonet fastener, solenoid, or other fastening device. In the example shown in FIG. 11, the locking mechanism 240 is a solenoid that, when activated, moves a pin 250 in the direction indicated by arrow A. With this arrangement, the solenoid can be activated to extend the pin 250 upwards so that the pin 250 engages with the sampling head 30. For example, the pin 250 can engage with an aperture 128 in the sampling head 30 (see FIG. 6(a)) to lock the sampling head 30 in position within the sample receiving device 200. Once analysis, or at least sample introduction, is complete, the solenoid can be activated to retract the pin 250 and allow the sampling head 30 to be removed from the sample receiving device 200. FIG. 10 shows a perspective view of the sample receiving device 200 with a control line 260 for the locking mechanism 240 and bracket 270 in exploded view. The bracket 270 can be used to fix the control line 260 to the sample receiving device 200.

Figure 8A:
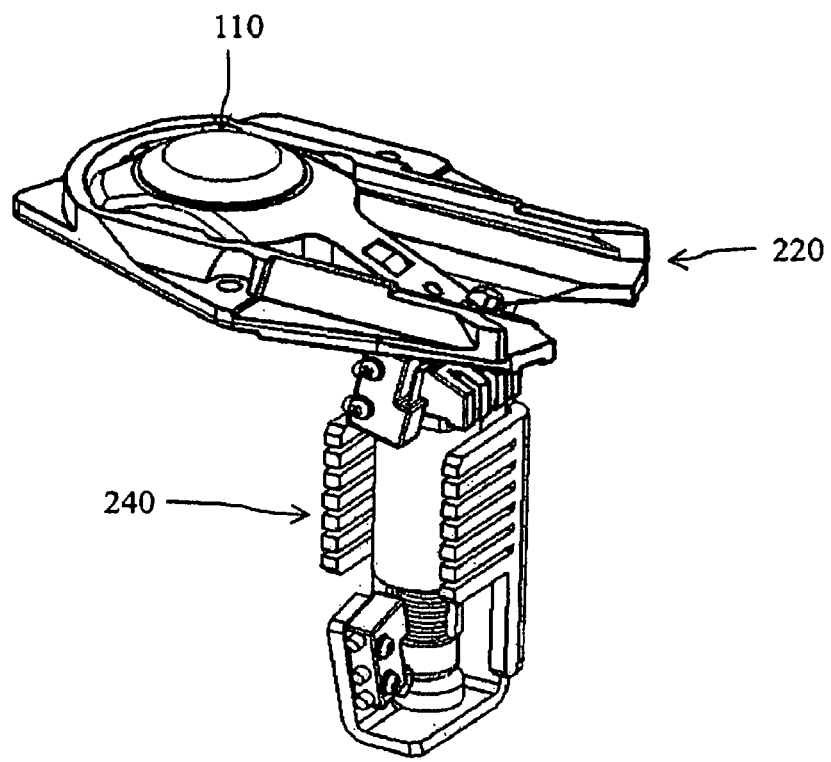
FIG. 8 shows (a) a perspective view and (b) an end view of an exemplary sampling head inserted into an exemplary sample receiving device.
Figure 8B:
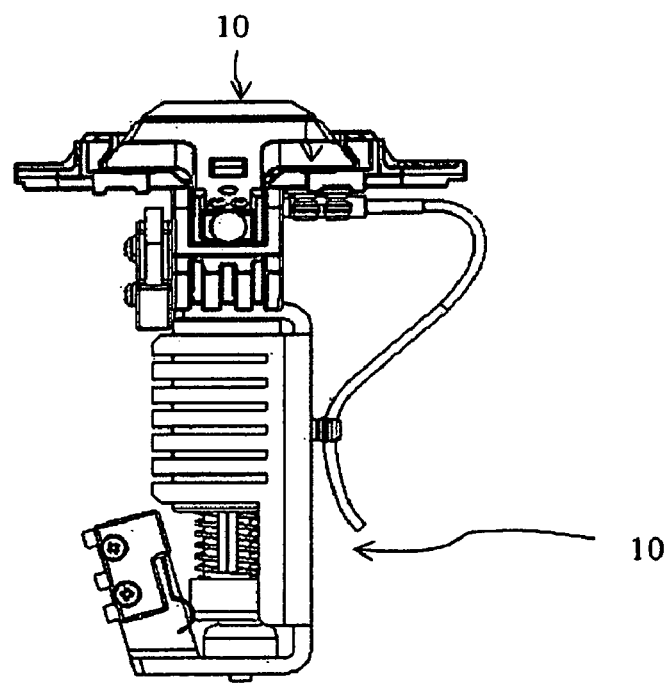

FIG. 8(a) shows a perspective view of a sampling head 30 that is positioned within the sample receiving device 200, while FIG. 8(b) shows an end view of a sampling device 10 that is positioned within the sample receiving device 200. In an embodiment, once an operator has used the sampling device 10 to position the sampling head 30 within the sample receiving device 200, the operator can detach the sampling head 30 from the body 20 of the sampling device 10, allowing an operator to attach an additional sampling head 30 to the sampling device 10 so that additional samples can be collected while the first sample is being analyzed. The operator can detach the sampling head 30 from the body 20 of the sampling device 10 by activating the connecting mechanism 80 that locks the sampling head 30 to the body 20 of the sampling device 10. Once analysis of a sample is complete, the operator can reattach the sampling head 30 to the body 20 of the sampling device 10 and remove the sampling head 30 from the analyzer.

The substrate 100 can be reused until the substrate 100 is dirty or damaged, at which point the substrate 100 can be replaced with a new substrate 100.

According to an embodiment, the sampling device 10 can include an incremental counter 11 that indicates the number of desorption cycles for a sampling head 30 and/or substrate 100. The incremental counter can include a display on the sampling head 30 or on the body 20 of the sampling device 10 that visually displays the number of desorption cycles to the operator. The incremental counter 11 can include a unique identifier that is positioned within the sampling head 30 or sampling frame 120. The unique identifier can be arranged to be detected by a counter or control system within the analyzer and/or body 20 of the sampling device 10 that counts the number of desorption cycles for the sampling head 30 and/or substrate 100. The counter or control system can then output the number of desorption cycles to the display of the sampling device 10, such as by wired or wireless transmission. For example, radio frequency signals can be used to transmit information between the unique identifier, counter or control unit, and display. The counter information can also be displayed on a device that is not the sampling device, such as, for example, an analytical device, a CPU, or other device capable of displaying the number of desorption cycles.

An incremental counter can be arranged to display a warning to the operator once the number of desorption cycles has reached a predetermined number indicating a limit for a sampling head 30 and/or substrate 100. Once this warning is displayed, the operator can replace the sampling head 30 and/or substrate 100 and reset the incremental counter. For example, the operator can reset the incremental counter by resetting the counter on the device or by resetting the counter on the analyzer. In one embodiment, the analyzer includes a touch screen which is used to reset the device.

According to an embodiment, the sampling device 10 can include a pressure sensor to indicate when a suitable amount of pressure is used in wiping an article to obtain a sample. The pressure sensor can include a warning device 90 that alerts the operator when the operator is employing insufficient pressure or excessive pressure during wiping or swabbing of an article with the sampling device 10 to collect a sample. The warning device 90 can be any suitable output device, such as, for example, a light indicator, a LCD screen, dial, or audible signal. In one embodiment, the pressure sensor can be used to warn the operator to use greater pressure during sample collection. For example, in one embodiment, the pressure sensor can be used to warn the operator to use greater pressure when wiping or swabbing surfaces of luggage to ensure proper surface contact and an efficient collection of sample material that might be found on the surfaces of the luggage. In another embodiment, the pressure sensor can be used to warn the operator when less than 2 pounds of force is applied, less than 1 pound of force is applied, or less than 0.5 pound of force is applied with the device.

According to an embodiment, the sampling device 10 includes a power supply. For example, the power supply can be a fixed, rechargeable power supply, a removeable rechargeable battery, or a disposable battery can be provided to power the pressure sensor and displays.

The substrate 100 can be used to collect samples of solid particles, aerosols, droplets and trace chemicals. The substrate 100 can be made of any suitable material. In one embodiment, the substrate 100 is Nomex®, Kevlar®, Teflon®, fiberglass, sharkskin, cotton, or combinations of these materials. The substrate can be coated or uncoated.

The sampling device 10 can be used with any suitable analyzers or analysis device, such as, for example, IMS, GC-IMS, IMS-IMS, or a dual IMS analyzer. In one embodiment a sample receiving device 200 is used in conjunction with a dual IMS analyzer. A sample can be introduced into the analyzer using any suitable method, such as, for example, desorption by thermal, infrared, or laser methods.

Given the disclosure of the present invention, one versed in the art would appreciate that there can be other embodiments and modifications within the scope and spirit of the invention. Accordingly, all modifications attainable by one versed in the art from the present disclosure within the scope and spirit of the disclosure are to be included as further embodiments.

What is claimed is:

1. A sampling device for collecting a sample on a substrate for analysis in an analyzer comprising:
    a body, and
    a sampling head arranged to hold the substrate,
    wherein the sampling device is arranged to be inserted into a sample receiving device so that the substrate is properly aligned within the analyzer for optimal or substantially optimal introduction of the sample into the analyzer, and
    wherein the sampling head is detachable from the body and the body is adapted to receive a second sampling head when the sampling head is detached.

2. The sampling device of claim 1, wherein the sampling head is arranged to remain within the analyzer during analysis of the sample.

3. The sampling device of claim 2, wherein the sampling device is arranged to attach a second sampling head to the body while the first sampling head remains within the analyzer.

4. The sampling device of claim 1, further comprising a connecting mechanism that attaches the sampling head to the body.

5. The sampling device of claim 1, wherein the sampling head includes an upper member and a lower member, and wherein the upper member and the lower member are arranged to hold the substrate between the upper member and the lower member.

6. The sampling device of claim 1, further comprising a counter that counts the number of desorption cycles for the sampling head.

7. The sampling device of claim 6, wherein the counter includes a display that displays the number of desorption cycles for the sampling head, and wherein the display is located on the sampling device or wherein the display is located on a device that is not the sampling device.

8. The sampling device of claim 1, further comprising a pressure sensor that detects the amount of pressure exerted by the sampling device on an item from which a sample is obtained during collection of a sample, and a warning device that alerts an operator when the operator is employing insufficient pressure during sample collection.

9. The sampling device of claim 1, further comprising a swing arm that includes a swing head and a surface that presses against a surface of the substrate.

10. The sampling device of claim 1, wherein the sampling head is arranged for thermal desorption or desorption via infrared radiation.

11. A sampling head for collecting a sample comprising:
    a sampling head arranged to hold a substrate,
    wherein the sampling head is arranged to be inserted into a sample receiving device so that the substrate is properly aligned within an analyzer for optimal or substantially optimal introduction of the sample into the analyzer, and
    wherein the sampling head can attach to a body of a sampling device and detach from the body of the sampling device at least twice to allow use of a single sampling device with multiple sampling heads.

12. The sampling head of claim 11, wherein the sampling head includes an upper member and a lower member, and wherein the upper member and the lower member are arranged to hold the substrate between the upper member and the lower member.

13. The sampling head of claim 11, further comprising a counter that counts the number of desorption cycles for the sampling head.

14. The sampling head of claim 11, further comprising a pressure sensor that detects the amount of pressure exerted by the sampling device on an item from which a sample is obtained during collection of a sample, and a warning device that alerts an operator when the operator is employing insufficient pressure during sample collection.

15. A method of collecting a sample comprising:
    mounting a substrate in a hand held sampling device that includes a body and a sampling head arranged to hold the substrate, wherein the sampling device is arranged to be inserted into a sample receiving device so that the substrate is properly aligned within the analyzer for optimal or substantially optimal introduction of the sample from the substrate, wherein the sampling head includes an upper member and a lower member, and wherein the upper member and the lower member are arranged to hold the substrate between the upper member and the lower member,
    manipulating the sampling device so that the substrate contacts a surface of interest, and inserting the sampling head into the analyzer.

16. A sampling device for collecting a sample on a substrate for analysis in an analyzer comprising:
a body, and
a sampling head arranged to hold the substrate, and
a connecting mechanism that attaches the sampling head to the body, wherein the connecting mechanism can attach the sampling head to the body, wherein the sampling device is arranged to be inserted into a sample receiving device so that the substrate is properly aligned within the analyzer for optimal or substantially optimal introduction of the sample into the analyzer, and wherein the sampling head is detachable from the body.

17. A sampling device for collecting a sample on a substrate for analysis in an analyzer comprising:
a body, and
a sampling head arranged to hold the substrate, and
a counter that counts the number of desorption cycles for the sampling head,
wherein the sampling device is arranged to be inserted into a sample receiving device so that the substrate is properly aligned within the analyzer for optimal or substantially optimal introduction of the sample into the analyzer, and
wherein the sampling head is detachable from the body.

18. The sampling device of claim 17, wherein the counter includes a display that displays the number of desorption cycles for the sampling head, and wherein the display is located on the sampling device or wherein the display is located on a device that is not the sampling device.

19. A sampling device for collecting a sample on a substrate for analysis in an analyzer comprising:
a body, and
a sampling head arranged to hold the substrate,
wherein the sampling device is arranged to be inserted into a sample receiving device so that the substrate is properly aligned within the analyzer for optimal or substantially optimal introduction of the sample into the analyzer,
wherein the sampling head includes an upper member and a lower member, and
wherein the upper member and the lower member are arranged to hold the substrate between the upper member and the lower member.

20. A sampling head for collecting a sample comprising:
a sampling head arranged to hold a substrate, and
a counter that counts the number of desorption cycles for the sampling head,
wherein the sampling head is arranged to be inserted into a sample receiving device so that the substrate is properly aligned within an analyzer for optimal or substantially optimal introduction of the sample into the analyzer.

21. The sampling head of claim 20, wherein the sampling head can attach to a body of a sampling device.

22. A sampling head for collecting a sample comprising:
a sampling head arranged to hold a substrate, and
a pressure sensor that detects the amount of pressure exerted by the sampling device on an item from which a sample is obtained during collection of a sample, and a warning device that alerts an operator when the operator is employing insufficient pressure during sample collection,
wherein the sampling head is arranged to be inserted into a sample receiving device so that the substrate is properly aligned within an analyzer for optimal or substantially optimal introduction of the sample into the analyzer.

23. The sampling head of claim 22, wherein the sampling head can attach to a body of a sampling device.

24. A sampling head for collecting a sample comprising:
a sampling head arranged to hold a substrate, and
a counter that counts the number of desorption cycles for the sampling head,
wherein the sampling head includes an upper member and a lower member,
wherein the upper member and the lower member are arranged to hold the substrate between the upper member and the lower member, and
wherein the sampling head is arranged to be inserted into a sample receiving device so that the substrate is properly aligned within an analyzer for optimal or substantially optimal introduction of the sample into the analyzer.

* * * * *